United States Patent [19]

Eibofner et al.

[11] 4,212,641
[45] Jul. 15, 1980

[54] DENTAL HANDPIECE

[75] Inventors: Eugen Eibofner, Biberach; Heinrich Reich, Hochdorf, both of Fed. Rep. of Germany

[73] Assignee: Kaltenbach & Voigt GmbH & Co., Biberach, Fed. Rep. of Germany

[21] Appl. No.: 837,639

[22] Filed: Sep. 28, 1977

[30] Foreign Application Priority Data

Oct. 1, 1976 [DE] Fed. Rep. of Germany ....... 2644458

[51] Int. Cl.$^2$ .............................................. A61C 1/12
[52] U.S. Cl. .................................................. 433/133
[58] Field of Search ....................... 32/26, 27; 128/305, 128/310; 433/133

[56] References Cited

U.S. PATENT DOCUMENTS 4,055,185  10/1977  Waldron ................................ 32/26

FOREIGN PATENT DOCUMENTS 2310737  10/1976  France ..................................... 32/27

Primary Examiner—Robert Peshock
Attorney, Agent, or Firm—Haseltine, Lake & Waters

[57] ABSTRACT

A dental handpiece comprising a holding sleeve, a head sleeve inclined to the holding sleeve and adapted to mount a dental instrument, a connecting zone providing an interconnection between the holding sleeve and the head sleeve, a drive shaft housed mainly within the holding sleeve and a driven shaft housed within the head sleeve, and a ball-type planetary transmission housed within the connecting zone and serving to transmit drive between the drive shaft and the driven shaft. The drive shaft is sub-divided into a first shaft portion which is housed in the holding sleeve, and a second shaft portion which is housed within the connecting zone and coupled with the planetary transmission. The second shaft portion extends coaxially with the driven shaft in the head sleeve, and the first and second drive shaft portions are coupled together by a rotary-drive-transmitting coupling.

7 Claims, 6 Drawing Figures

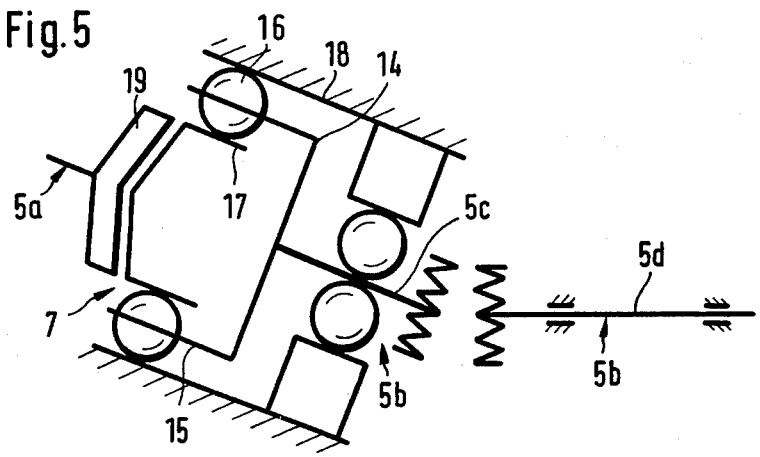
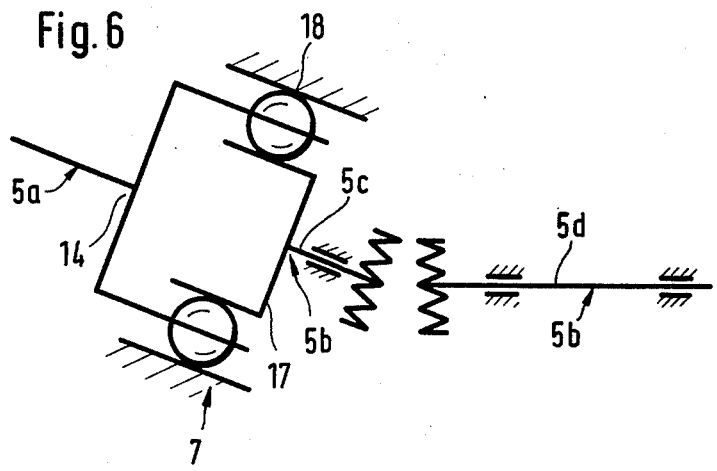

DENTAL HANDPIECE

This invention relates to a dental handpiece comprising a holding sleeve, a head sleeve inclined to the holding sleeve and adapted to mount a dental instrument, a connecting zone providing an interconnection between the holding sleeve and the head sleeve, a drive shaft arranged within the holding sleeve, a driven shaft arranged within the head sleeve, and a ball-type planetary transmission arranged in the connecting zone and providing a drive-connection between the drive shaft and the driven shaft.

A dental handpiece of the above type forms the subject of U.S. patent application Ser. No. 684,453 which was filed on May 7, 1976 and is now U.S. Pat. No. 4,047,301 issued Sept. 13, 1977 in the name of Eugen Eibofner and is assigned to the assignee of this application.

In the dental handpiece, one of the shaft portions engages in the manner of a cage, with the balls of the planetary transmission, the balls being mounted with frictional engagement between an inner ring and an outer ring, and one of these rings being arranged to be non-rotatable and the other ring being arranged on the other shaft portion to be rotatable therewith. In one embodiment, the limbs of the cage provided on one shaft portion extend parallel to the longitudinal axis of the driven shaft portion and thus include with the axis of the drive shaft portion an angle corresponding to the angle of inclination between the holding sleeve and the head sleeve. Since, therewith, the plane extending through the centre-points of the balls of the transmission extends perpendicular to the axis of the driven shaft portion, the balls must, on each drive shaft rotation, slide to and fro parallel to the axis of the driven shaft portion and along the cage edges laterally delimiting the cage slots in which the balls are held. This axial movement of the balls brings about, with reference to the cage and the balls, a relatively high degree of heating, a considerable degree of wear and also an increase in noise.

It is an object of the invention to provide a dental handpiece in which the above problems can be avoided.

According to the invention there is provided a dental handpiece comprising:
a holding sleeve;
a head sleeve inclined to the holding sleeve and adapted to mount a dental instrument;
a connecting zone providing an interconnection between said holding sleeve and said head sleeve;
a drive shaft arranged in said holding sleeve;
a driven shaft arranged in said head sleeve;
and a ball-type planetary transmission arranged in the connecting zone and providing a drive-transmitting connection between said drive shaft and said driven shaft;
in which said drive shaft comprises a first shaft portion arranged in said holding sleeve, a second portion arranged in said connecting zone, and a rotary-drive transmitting coupling arranged to couple said first and second shaft portions together, said second shaft portion being coupled with said ball-type planetary transmission and being arranged co-axially with said driven shaft in said head sleeve.

The balls of the planetary transmission do not vary their positions axially relative to the driven shaft, during rotation of the driveshaft, i.e. they no longer slide along the edge of a cage of the transmission so that the adverse consequences described above are avoided, and quiet running of the transmission can be achieved. Furthermore, this is obtainable without requiring any enlargement or no substantial enlargement, of the handpiece diameter.

Also the drive-transmitting coupling will operate quietly, if it comprises, as is preferred, in space-saving manner a respective spur gear wheel arranged at each of the two ends facing each other of the first and second shaft portions. The spur gears may have a transmission or reduction ratio from 1:2 to 2:1, and preferably 1:1.

The cage meshing with the balls of the planetary transmission may be arranged at the end of the second shaft portion adjacent the planetry transmission, or at the end of the driven shaft adjacent the planetary transmission. In the former case, it is expedient if the second shaft portion has a bearing which forms a unit with the planetary transmission. In this way, there is produced an especially small, compact construction which is also readily manipulated for purposes of assembly or replacement, in the manner of a cartridge, comprising the second shaft portion inclusive of the bearings thereof and also the end thereof which is of cage-like design, the balls and their outer ring and inner ring of the planetary transmission. Falling-out of the balls of the planetary transmission out of this structural unit may be prevented by providing annular grooves in the inner wall of the outer ring and in the outer wall of the inner ring, in which grooves the balls are arranged. The same applies to the mounting of the second shaft portion, in particular if this mounting is constituted by ball bearings.

The aforementioned compact structural unit can be still better manipulated if the mounting of the second shaft portion and the planetary transmission are held together by, and housed within an encasing sleeve. The cage-like end meshing with the balls of one of the drive-shaft portions can be designed as an open cage in the manner of a round fork or as an open cage in the manner of a round fork or as a pot-like, closed cage having at its ends closed cage apertures, with which arrangement the cage apertures provided in the cage walls must not be of slot-like design but only adapted to the diameter of the balls i.e. requiring to be substantially round, since the said axial movement of the balls (as stated) no longer takes place.

BRIEF DESCRIPTION OF THE DRAWINGS

FIGS. 5 and 6 are schematic illustrations of alternative arrangements of the planetary transmission.

DESCRIPTION OF THE PREFERRED EMBODIMENTS

Figure 1:
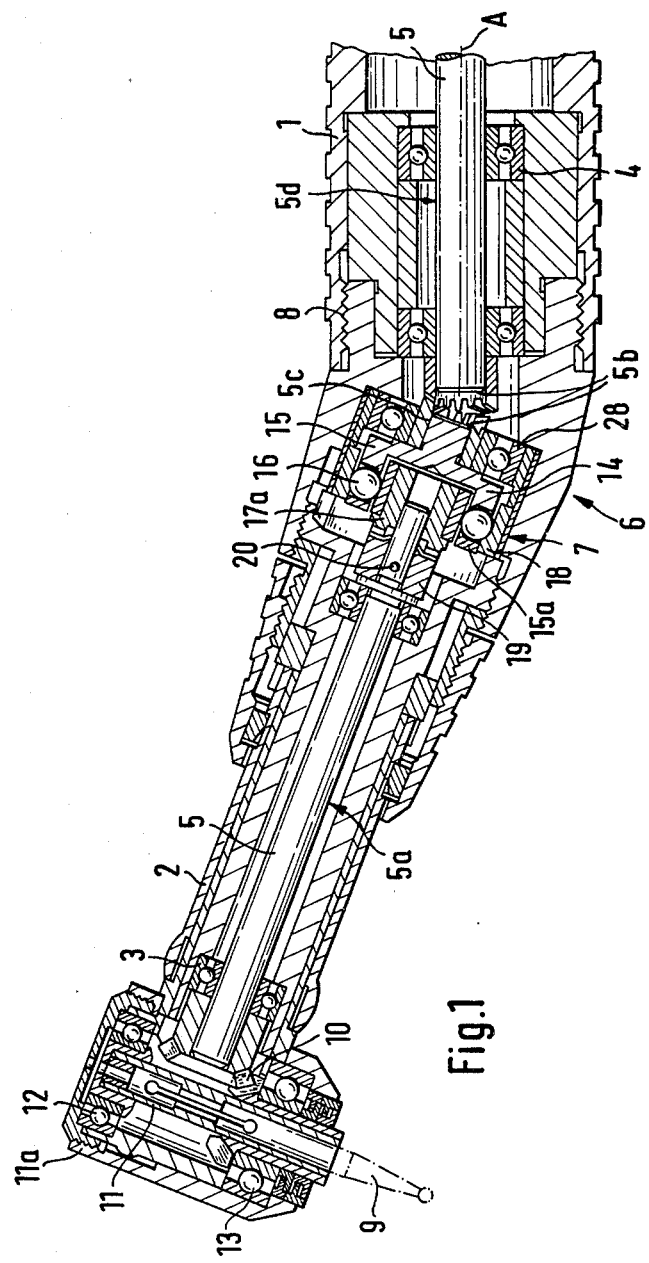
FIG. 1 is a longitudinal sectional view of the tool-holding end of an angled dental handpiece according to the invention.

The angled dental handpiece shown in FIG. 1 comprises a holding sleeve 1 and a headsleeve 2 inclined relative to the longitudinal axis A of the sleeve 1. A two-part driveshaft 5 is mounted in the handpiece with the aid of bearings 3, 4 and is transversely divided in the zone of a bending location 6 between sleeves 1 and 2. The two driveshaft portions or elements 5a and 5b are housed respectively in the sleeves 2 and 1 and are interengaged by a ball-type planetary transmission 7. The sleeve 1 and the head sleeve 2 constitute two independent portions or elements which are releasably connected with each other by a screwthread 8.

The shaft element 5a mounted in the head sleeve 2 is driven by the driving shaft element 5b via the transmission 7, and serves for driving a dental instrument 9, for example a drill. For this purpose, the element 5a engages via a toothed gearing 10 with a drive sheeve 11 containing the instrument 9 and arranged at right angles to the drive shaft element 5a, the bearings of the drive sleeve 11 being arranged in angle head 11a and designated 12 and 13.

The planetary transmission 7 can be variously designed as FIGS. 5 and 6 show diagrammatically. The transmission according to FIG. 5 corresponds in construction to the embodiment according to FIGS. 1 and 2 whereby transmission from the shaft element 5b to the shaft element 5a takes place in the ratio 1:2.7. FIG. 6 shows an embodiment of reduction gearing.

The planetary transmission 7 comprises balls 16 which are located between an inner ring 17 and an outer ring 18. A cage having webs 15 engages the balls 16 and is driven by a shaft end 14. The shaft end 14 (facing the planetary transmission) of the driveshaft element 5b in FIGS. 1, 2 and 5 or of the shaft elements 5a in FIG. 6 is according to FIGS. 1 and 2 designed as a closed pot-like cage having at its ends 15a closed cage apertures 15b. With the cage webs 15, the shaft end 14 engages between the balls 16 of the transmission 7. The balls 16 are, according to FIG. 2, mounted by frictional engagement between the inner ring 17 and the outer ring 18. The outer ring 18 is arranged to be non-rotatable, whereas the inner ring 17 (according to FIGS. 1, 2 and 5) is arranged to be rotatable on the shaft element 5a.

Figure 2:
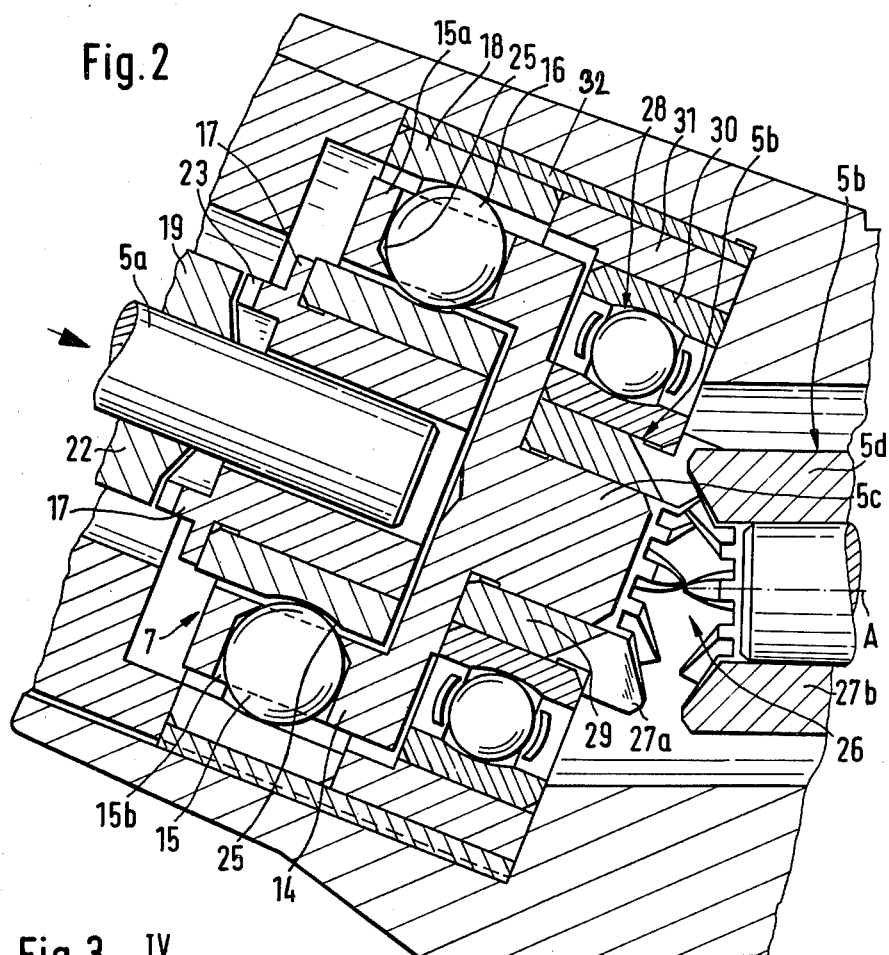
FIG. 2 is an enlarged view of a ball-type planetary transmission provided in the handpiece.

Referring to FIGS. 1, 2 and 5, the inner ring 17 (rotatable with the shaft element 5a) is axially and rotatably displaceable under the influence of a displacement ring 19 which is secured by means of a crosspin 20 on the shaft element 5a.

Figure 3:
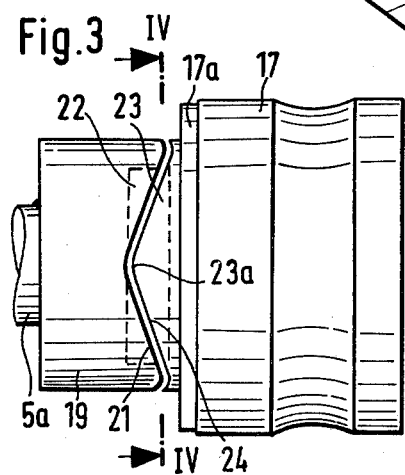
FIG. 3 is a detail side view of the handpiece.
Figure 4:
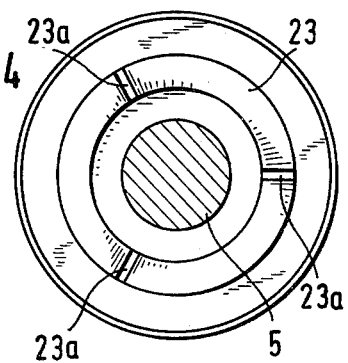
FIG. 4 is a sectional view taken on the line IV—IV in FIG. 3.

For this purpose, the displacement ring 19 is, in particular according to FIGS. 2 to 4, provided with oblique toothing 22 having straight and/or curved tooth flanks 21, which oblique toothing meshes with corresponding oblique toothing 23 having tooth flanks 24 on the axially moveable inner ring 17. Referring to FIG. 4, three teeth are arranged. The teeth apices of the oblique toothing 23 are designated 23a in FIG. 4.

If in the case of the embodiment according to FIGS. 1, 2 and 5, the instrument 9 is loaded inasmuch as its rotation is prevented or retarded, for example at the tooth to be treated, then the relative rotation resulting therefrom of the two shaft elements 5a and 5b, and therewith of the displacement ring 19 and of the inner ring 17, has the result that the tooth flanks 21, 24 of the two oblique toothings 22, 23 slide at each other in the sense of a displacement of the inner ring 17 taking place in the axial direction on the driveshaft element 5a, so that automatic adjustment takes place of the balls 16 which are mounted in annular grooves 25 formed in the inner ring 17 and the outer ring 18.

Referring to FIGS. 1 to 3, the inner ring 17 is secured to an inner sleeve 17a, at which the oblique toothing 23 is provided and which is arranged jointly with the inner ring 17 to be axially displaceable and rotatable on the shaft element 5a.

As will be apparent from FIGS. 1, 2, 5 and 6, the shaft element 5b is transversely divided closely adjacent its end 14 (facing the planetary transmission) which, in the case of the embodiment according to FIGS. 1,2 and 5, has the cage webs 15. The shaft element 5b is thus subdivided into two shaft sections 5c, 5d which are coupled together by a coupling 26 which enables the shaft sections 5c and 5d to rotate together. The shaft section 5c, which faces the transmission 7, is arranged coaxially with the shaft element 5a, which is driven by the planetary transmission 7.

The coupling 26 comprises spur gear wheels 27a and 27b arranged respectively at the two facing ends of the shaft sections 5c, 5d.

The shaft section 5c is mounted in a ball bearing 28, comprising an inner race secured to a sleeve 29 having the spur gear 27a (see FIG. 2), the sleeve 29 being secured on the shaft section 5c. The outer race 30 of the ball bearing 28 is secured in an insert ring 31 the outer surface of which is flush with the outer surface of the outer ring 18 of the planetary transmission 7. The outer ring 18 and the insert ring 31 are secured in an encasing sleeve 32 which holds together the entire ball bearing 28 with the shaft section 5c and the transmission 7, including inner ring 17, 17a, thereby forming a cartridge-like structural unit.

The longitudinal extent of the element of the shaft section 5c adjacent the cage webs 15, and provided with the spur gear 27a, need only be sufficient to accommodate the ball bearing 28. Due to the shortness achieved in this manner of the shaft section 5c, which is coaxial with the driven driveshaft element 5a, the smallest possible dimensions are achieved for the cartridge-like structural unit and this contributes to avoiding an enlargement of the handpiece diameter in the zone of the bending location 6.

We claim:

1. A dental handpiece comprising: a holding sleeve; a head sleeve inclined to the holding sleeve at an obtuse angle and adapted to mount a dental instrument; a connecting zone providing an interconnection between said holding sleeve and said head sleeve; a drive shaft arranged in said holding sleeve; a drive shaft arranged in said head sleeve; and a ball-type planetary transmission arranged in the connecting zone wholly immediately adjacent to a bisector of said obtuse angle formed between axes of said head sleeve and of said holding sleeve in a straight portion of said head sleeve, said planetary transmission providing a drive-transmitting connection between said drive shaft and said driven shaft; said drive shaft comprising first shaft portion arranged in said holding sleeve, a second shaft portion arranged in said connecting zone, said second shaft portion comprising a driven portion of a rotary-drive transmitting coupling arranged to couple said first and second shaft portions together, said second shaft portion being part of said ball-type planetary transmission and being arranged coaxially with said driven shaft in said head sleeve.

2. A dental handpiece according to claim 1, wherein said rotary-drive transmitting coupling comprises interengaging spur gears provided on the adjacent ends of said first and second shaft portions.

3. A dental handpiece according to claim 1, wherein said planetary transmission includes a cage engaging the balls of said transmission, said cage being coupled with said second shaft portion, and in which a bearing is provided which mounts said second shaft portion and which forms a unit with said planetary transmission.

4. A dental handpiece according to claim 3, wherein said bearing comprises a ball bearing.

5. A dental handpiece according to claim 3, including a sleeve forming a housing for said bearing and for said transmission.

6. A dental handpiece according to claim 1 wherein said rotary-drive transmitting coupling comprises interengaging spur gears on the adjacent ends of said first and second shaft portions, said planetary transmission including a cage engaging the balls of said transmission, said cage being coupled with said second shaft portion, and a bearing mounting said second shaft portion and forming a unit with said planetary transmission, said bearing comprising a ball bearing, and a sleeve forming a housing for said bearing and for said transmission.

7. A dental handpiece according to claim 1 wherein said planetary transmission is located adjacent said head sleeve, said coupling transmitting force at the bend location, said coupling having a driven portion which is also the driving portion of a cage of said planetary transmission so that the driven portion of the coupling is also part of the planetary transmission, the bend holding both the planetary transmission and the coupling.

* * * * *